United States Patent
Ooshima

(10) Patent No.: US 7,824,917 B2
(45) Date of Patent: Nov. 2, 2010

(54) METHOD OF DETECTING NUCLEIC ACID BY USING NUCLEIC ACID MICROARRAY

(75) Inventor: Hiroyuki Ooshima, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 299 days.

(21) Appl. No.: 11/815,239

(22) PCT Filed: Feb. 6, 2006

(86) PCT No.: PCT/JP2006/302402

§ 371 (c)(1),
(2), (4) Date: Aug. 1, 2007

(87) PCT Pub. No.: WO2006/083040

PCT Pub. Date: Aug. 10, 2006

(65) Prior Publication Data

US 2009/0011513 A1  Jan. 8, 2009

(30) Foreign Application Priority Data

Feb. 4, 2005  (JP) .............................. 2005-028843

(51) Int. Cl.
*C12Q 1/68* (2006.01)
*C07H 21/00* (2006.01)

(52) U.S. Cl. .................... 436/94; 436/174; 436/175; 435/6; 536/23.1

(58) Field of Classification Search .................... 436/63, 436/94, 174, 175; 435/6; 536/23.1
See application file for complete search history.

(56) References Cited

U.S. PATENT DOCUMENTS

| 2002/0022226 A1 | 2/2002 | Nakao et al. |
| 2002/0110903 A1* | 8/2002 | Iwaki et al. .............. 435/287.2 |
| 2002/0187476 A1* | 12/2002 | Koroulis et al. ................ 435/6 |
| 2005/0079501 A1 | 4/2005 | Koike et al. |
| 2007/0264630 A1 | 11/2007 | Gumbrecht et al. |

FOREIGN PATENT DOCUMENTS

| EP | 1132485 A2 | 9/2001 |
| EP | 1469067 A1 | 10/2004 |
| JP | 2003-028767 A | 1/2003 |
| JP | 2003-329685 A | 11/2003 |

(Continued)

OTHER PUBLICATIONS

English language translation of JP 2003-028767, Jan. 29, 2003.*

(Continued)

*Primary Examiner*—Maureen M Wallenhorst
(74) *Attorney, Agent, or Firm*—McDermott Will & Emery LLP

(57) ABSTRACT

The present invention provides a method of detecting a nucleic acid which is not restricted by the design of the base sequence of a nucleic acid probe. By repeating washing and detection in multiple stages, the present invention can improve the precision of sequence-specific hybridization stepwise and also can ease restrictions in designing the nucleic acid probes, in particular, restrictions on the Tm value (the temperature at which the nucleic acid double strand is dissociated into single strands) or the sequence length of the nucleic acid probes.

4 Claims, 4 Drawing Sheets

| B | B | B | B | B | B | B | B | B | B | B | B |
|---|---|---|---|---|---|---|---|---|---|---|---|
| B | B | B | B | B | B | B | B | B | B | B | B |
| B | B | B | B | B | B | B | B | B | B | B | B |
| B | B | B | B | B | B | B | B | B | B | B | B |
| B | B | B | 11 | 12 | 13 | 14 | 15 | B | B | B | B |
| B | B | B | 21 | 22 | 23 | 24 | 25 | B | B | B | B |
| B | B | B | 16 | 17 | 18 | 19 | 20 | B | B | B | B |
| B | B | B | 26 | 27 | 28 | 29 | 30 | B | B | B | B |
| B | B | B | B | B | B | B | B | B | B | B | B |
| B | B | B | B | B | B | B | B | B | B | B | B |
| B | B | B | B | B | B | B | B | B | B | B | B |
| B | B | B | B | B | B | B | B | B | B | B | B |

FOREIGN PATENT DOCUMENTS

WO           2004106546 A1    12/2004

OTHER PUBLICATIONS

Urakawa H. et al. "Optimization of single-base-pair mismatch discrimination in oligonucleotide microarrays". Applied and Environmental Microbiology, American Society for Microbiology, US, vol. 69, No. 5, May 1, 2003, pp. 2848-2856, XP002295900, ISSN: 0099-2240.

David F. et al. "Detection and typing of human papillomavirus DNA from cervical biopsies by the slot-blot hydridization method", Molecular and Cellular Probes, Academic Press, London, GB, vol. 4, No. 1, Feb. 1, 1990, pp. 53-61, XP024865930, ISSN:0890-8508.

Sambrook J. et al. "Hybridization of radiolabeled probes to nucleic acids immobilized on nitrocellulose filters or nylon membranes", Molecular Cloning, A Laboratory Manual, vol. 2, Jan. 1, 1989, pp. 9.52-9.55; XP002070958.

Benes V. et al. "Standardization of protocols in cDNA microarray analysis" Trends in Biochemical Sciences, Elsevier, Haywards, GB, vol. 28, No. 5, May 1, 2003, pp. 244-249; XP004425563, ISSN: 0968-0004.

\* cited by examiner

Figure 2

| | | | | | | | | | | | |
|---|---|---|---|---|---|---|---|---|---|---|---|
| B | B | B | B | B | B | B | B | B | B | B | B |
| B | B | B | B | B | B | B | B | B | B | B | B |
| B | B | B | B | B | B | B | B | B | B | B | B |
| B | B | B | B | B | B | B | B | B | B | B | B |
| B | B | B | 11 | 12 | 13 | 14 | 15 | B | B | B | B |
| B | B | B | 21 | 22 | 23 | 24 | 25 | B | B | B | B |
| B | B | B | 16 | 17 | 18 | 19 | 20 | B | B | B | B |
| B | B | B | 26 | 27 | 28 | 29 | 30 | B | B | B | B |
| B | B | B | B | B | B | B | B | B | B | B | B |
| B | B | B | B | B | B | B | B | B | B | B | B |
| B | B | B | B | B | B | B | B | B | B | B | B |
| B | B | B | B | B | B | B | B | B | B | B | B |

```
                        SEQUENCE LISTING

<160> NUMBER OF SEQ ID NOS: 42

<210> SEQ ID NO 1
<211> LENGTH: 66
<212> TYPE: DNA
<213> ORGANISM: Artificial
<220> FEATURE:
<223> OTHER INFORMATION: Synthetic DNA

<400> SEQUENCE: 1
cggattaggg cgtttttttat tttcgtcggg agttcgtcga ttggttgggt gtgggcgtac      60
gtgatc                                                                 66

<210> SEQ ID NO 2
<211> LENGTH: 63
<212> TYPE: DNA
<213> ORGANISM: Artificial
<220> FEATURE:
<223> OTHER INFORMATION: Synthetic DNA

<400> SEQUENCE: 2
cgtttttggt gagcgtcgtc gttagttaat cgcggggcgt agaggttttt ggtttcgttt      60
cgc                                                                    63

<210> SEQ ID NO 3
<211> LENGTH: 58
<212> TYPE: DNA
<213> ORGANISM: Artificial
<220> FEATURE:
<223> OTHER INFORMATION: Synthetic DNA

<400> SEQUENCE: 3
cggcgtgggt gtggggcgag tgggtgtgtg cggggtgtgc gcggtagagc gcgttagc        58
```

```
<210> SEQ ID NO 4
<211> LENGTH: 60
<212> TYPE: DNA
<213> ORGANISM: Artificial
<220> FEATURE:
<223> OTHER INFORMATION: Synthetic DNA

<400> SEQUENCE: 4
cggggggcgg tgtttcgggg tttatttggt tgtagttacg tatttttttt tagtggcgtc    60

<210> SEQ ID NO 5
<211> LENGTH: 77
<212> TYPE: DNA
<213> ORGANISM: Artificial
<220> FEATURE:
<223> OTHER INFORMATION: Synthetic DNA

<400> SEQUENCE: 5
cgcgcgttcg tcgttcgtta tatatcgttc gtagtattcg tgtttagttt cgtagtggcg    60
tttgacgtcg cgttcgc                                                   77

<210> SEQ ID NO 6
<211> LENGTH: 54
<212> TYPE: DNA
<213> ORGANISM: Artificial
<220> FEATURE:
<223> OTHER INFORMATION: Synthetic DNA

<400> SEQUENCE: 6
cggatcgagt gcgttcggcg gttgcggaga ggggtagagt aggtagcggg cggc          54

<210> SEQ ID NO 7
<211> LENGTH: 61
<212> TYPE: DNA
<213> ORGANISM: Artificial
<220> FEATURE:
<223> OTHER INFORMATION: Synthetic DNA

<400> SEQUENCE: 7
cgcgtggtgt tttgcggtcg tcgtcgttgt ggtcgttcgg ggtggggtgt gaggagggga    60
c                                                                    61

<210> SEQ ID NO 8
<211> LENGTH: 61
<212> TYPE: DNA
<213> ORGANISM: Artificial
<220> FEATURE:
<223> OTHER INFORMATION: Synthetic DNA

<400> SEQUENCE: 8
cggttggggt ttcgcgttta tacggttttt ggcgggggtt cgcgcgtttc gggagtttcg    60
c                                                                    61

<210> SEQ ID NO 9
<211> LENGTH: 64
<212> TYPE: DNA
<213> ORGANISM: Artificial
<220> FEATURE:
<223> OTHER INFORMATION: Synthetic DNA

<400> SEQUENCE: 9
cggagcgacg cgtcgtatag ttaatcggcg gagttttat cgcgggtatt tcggtggcgt    60
tcgc                                                                 64
```

<210> SEQ ID NO 10
<211> LENGTH: 63
<212> TYPE: DNA
<213> ORGANISM: Artificial
<220> FEATURE:
<223> OTHER INFORMATION: Synthetic DNA

<400> SEQUENCE: 10
cgcgggcggc gtcgtcgaac gttagcgtta gggggcgggg tggggagggg agcgaggttt    60
ttc                                                                  63

<210> SEQ ID NO 11
<211> LENGTH: 66
<212> TYPE: DNA
<213> ORGANISM: Artificial
<220> FEATURE:
<223> OTHER INFORMATION: Synthetic DNA

<400> SEQUENCE: 11
gatcacgtac gcccacaccc aaccaatcga cgaactcccg acgaaaataa aaaacgccct    60
aatccg                                                               66

<210> SEQ ID NO 12
<211> LENGTH: 63
<212> TYPE: DNA
<213> ORGANISM: Artificial
<220> FEATURE:
<223> OTHER INFORMATION: Synthetic DNA

<400> SEQUENCE: 12
gcgaaacgaa accaaaaacc tctacgcccc gcgattaact aacgacgacg ctcaccaaaa    60
acg                                                                  63

<210> SEQ ID NO 13
<211> LENGTH: 58
<212> TYPE: DNA
<213> ORGANISM: Artificial
<220> FEATURE:
<223> OTHER INFORMATION: Synthetic DNA

<400> SEQUENCE: 13
gctaacgcgc tctaccgcgc acacccgca cacacccact cgccccacac ccacgccg       58

<210> SEQ ID NO 14
<211> LENGTH: 60
<212> TYPE: DNA
<213> ORGANISM: Artificial
<220> FEATURE:
<223> OTHER INFORMATION: Synthetic DNA

<400> SEQUENCE: 14
gacgccacta aaaaaaaata cgtaactaca accaaataaa ccccgaaaca ccgccccccg    60

<210> SEQ ID NO 15
<211> LENGTH: 77
<212> TYPE: DNA
<213> ORGANISM: Artificial
<220> FEATURE:
<223> OTHER INFORMATION: Synthetic DNA

<400> SEQUENCE: 15
gcgaacgcga cgtcaaacgc cactacgaaa ctaaacacga atactacgaa cgatatataa    60

-continued cgaacgacga acgcgcg                                                77

<210> SEQ ID NO 16
<211> LENGTH: 54
<212> TYPE: DNA
<213> ORGANISM: Artificial
<220> FEATURE:
<223> OTHER INFORMATION: Synthetic DNA

<400> SEQUENCE: 16
gccgcccgct acctactcta cccctctccg caaccgccga acgcactcga tccg        54

<210> SEQ ID NO 17
<211> LENGTH: 61
<212> TYPE: DNA
<213> ORGANISM: Artificial
<220> FEATURE:
<223> OTHER INFORMATION: Synthetic DNA

<400> SEQUENCE: 17
gtcccctcct cacaccccac cccgaacgac cacaacgacg acgaccgcaa aacaccacgc  60
g                                                                 61

<210> SEQ ID NO 18
<211> LENGTH: 61
<212> TYPE: DNA
<213> ORGANISM: Artificial
<220> FEATURE:
<223> OTHER INFORMATION: Synthetic DNA

<400> SEQUENCE: 18
gcgaaactcc cgaaacgcgc gaaccccgc caaaaaccgt ataaacgcga aaccccaacc  60
g                                                                 61

<210> SEQ ID NO 19
<211> LENGTH: 64
<212> TYPE: DNA
<213> ORGANISM: Artificial
<220> FEATURE:
<223> OTHER INFORMATION: Synthetic DNA

<400> SEQUENCE: 19
gcgaacgcca ccgaaatacc cgcgataaaa actccgccga ttaactatac gacgcgtcgc  60
tccg                                                              64

<210> SEQ ID NO 20
<211> LENGTH: 63
<212> TYPE: DNA
<213> ORGANISM: Artificial
<220> FEATURE:
<223> OTHER INFORMATION: Synthetic DNA

<400> SEQUENCE: 20
gaaaaacctc gctccctccc ccaccccgcc ccctaacgct aacgttcgac gacgccgccc  60
gcg                                                               63

<210> SEQ ID NO 21
<211> LENGTH: 66
<212> TYPE: DNA
<213> ORGANISM: Artificial
<220> FEATURE:
<223> OTHER INFORMATION: Synthetic DNA

<400> SEQUENCE: 21

```
aatcacatac acccacaccc aaccaatcaa caaactccca acaaaaataa aaaacaccct    60
aatcca                                                              66

<210> SEQ ID NO 22
<211> LENGTH: 63
<212> TYPE: DNA
<213> ORGANISM: Artificial
<220> FEATURE:
<223> OTHER INFORMATION: Synthetic DNA

<400> SEQUENCE: 22
acaaaacaaa accaaaaacc tctacacccc acaattaact aacaacaaca ctcaccaaaa    60
aca                                                                 63

<210> SEQ ID NO 23
<211> LENGTH: 58
<212> TYPE: DNA
<213> ORGANISM: Artificial
<220> FEATURE:
<223> OTHER INFORMATION: Synthetic DNA

<400> SEQUENCE: 23
actaacacac tcatccacac accccaca cacacccact caccccacac ccacacca       58

<210> SEQ ID NO 24
<211> LENGTH: 60
<212> TYPE: DNA
<213> ORGANISM: Artificial
<220> FEATURE:
<223> OTHER INFORMATION: Synthetic DNA

<400> SEQUENCE: 24
aacaccacta aaaaaaaata cataactaca accaaataaa ccccaaaaca ccaccccca    60

<210> SEQ ID NO 25
<211> LENGTH: 77
<212> TYPE: DNA
<213> ORGANISM: Artificial
<220> FEATURE:
<223> OTHER INFORMATION: Synthetic DNA

<400> SEQUENCE: 25
acaaacacaa catcaaacac cactacaaaa ctaaacacaa atactacaaa caatatataa    60
caaacaacaa acacaca                                                  77

<210> SEQ ID NO 26
<211> LENGTH: 54
<212> TYPE: DNA
<213> ORGANISM: Artificial
<220> FEATURE:
<223> OTHER INFORMATION: Synthetic DNA

<400> SEQUENCE: 26
accacccact acctactcta cccctatcca caaccaccaa acacactcaa tcca          54

<210> SEQ ID NO 27
<211> LENGTH: 61
<212> TYPE: DNA
<213> ORGANISM: Artificial
<220> FEATURE:
<223> OTHER INFORMATION: Synthetic DNA

<400> SEQUENCE: 27
```

```
atccctcct cacaccccac cccaaacaac cacaacaaca acaaccacaa aacaccacac        60
a                                                                      61
```

<210> SEQ ID NO 28
<211> LENGTH: 61
<212> TYPE: DNA
<213> ORGANISM: Artificial
<220> FEATURE:
<223> OTHER INFORMATION: Synthetic DNA

<400> SEQUENCE: 28

```
acaaaactcc caaacacac aaccccac caaaaccat ataaacacaa aaccccaacc           60
a                                                                      61
```

<210> SEQ ID NO 29
<211> LENGTH: 64
<212> TYPE: DNA
<213> ORGANISM: Artificial
<220> FEATURE:
<223> OTHER INFORMATION: Synthetic DNA

<400> SEQUENCE: 29

```
acaaacacca ccaaaatacc cacaataaaa actccaccaa ttaactatac aacacatcac       60
tcca                                                                   64
```

<210> SEQ ID NO 30
<211> LENGTH: 63
<212> TYPE: DNA
<213> ORGANISM: Artificial
<220> FEATURE:
<223> OTHER INFORMATION: Synthetic DNA

<400> SEQUENCE: 30

```
aaaaaacctc actccctccc ccaccccacc ccctaacact aacattcaac aacaccaccc       60
aca                                                                    63
```

<210> SEQ ID NO 31
<211> LENGTH: 22
<212> TYPE: DNA
<213> ORGANISM: Artificial
<220> FEATURE:
<223> OTHER INFORMATION: Synthetic DNA

<400> SEQUENCE: 31

```
tgaggtagta ggttgtgtgg tt                                               22
```

<210> SEQ ID NO 32
<211> LENGTH: 22
<212> TYPE: DNA
<213> ORGANISM: Artificial
<220> FEATURE:
<223> OTHER INFORMATION: Synthetic DNA

<400> SEQUENCE: 32

```
tgaggtagta ggttgtatgg tt                                               22
```

<210> SEQ ID NO 33
<211> LENGTH: 21
<212> TYPE: DNA
<213> ORGANISM: Artificial
<220> FEATURE:
<223> OTHER INFORMATION: Synthetic DNA

<400> SEQUENCE: 33
agaggtagta ggttgcatag t                                    21

<210> SEQ ID NO 34
<211> LENGTH: 21
<212> TYPE: DNA
<213> ORGANISM: Artificial
<220> FEATURE:
<223> OTHER INFORMATION: Synthetic DNA

<400> SEQUENCE: 34
tgaggtagga ggttgtatag t                                    21

<210> SEQ ID NO 35
<211> LENGTH: 21
<212> TYPE: DNA
<213> ORGANISM: Artificial
<220> FEATURE:
<223> OTHER INFORMATION: Synthetic DNA

<400> SEQUENCE: 35
tgaggtagta gattgtatag t                                    21

<210> SEQ ID NO 36
<211> LENGTH: 21
<212> TYPE: DNA
<213> ORGANISM: Artificial
<220> FEATURE:
<223> OTHER INFORMATION: Synthetic DNA

<400> SEQUENCE: 36
tgaggtagta gtttgtacag t                                    21

<210> SEQ ID NO 37
<211> LENGTH: 22
<212> TYPE: DNA
<213> ORGANISM: Artificial
<220> FEATURE:
<223> OTHER INFORMATION: Synthetic DNA

<400> SEQUENCE: 37
aaccacacaa cctactacct ca                                   22

<210> SEQ ID NO 38
<211> LENGTH: 22
<212> TYPE: DNA
<213> ORGANISM: Artificial
<220> FEATURE:
<223> OTHER INFORMATION: Synthetic DNA

<400> SEQUENCE: 38
aaccatacaa cctactacct ca                                   22

<210> SEQ ID NO 39
<211> LENGTH: 21
<212> TYPE: DNA
<213> ORGANISM: Artificial
<220> FEATURE:
<223> OTHER INFORMATION: Synthetic DNA

<400> SEQUENCE: 39
actatgcaac ctactacctc t                                    21

<210> SEQ ID NO 40
<211> LENGTH: 21
<212> TYPE: DNA

```
<213> ORGANISM: Artificial
<220> FEATURE:
<223> OTHER INFORMATION: Synthetic DNA

<400> SEQUENCE: 40
actatacaac ctcctacctc a                                              21

<210> SEQ ID NO 41
<211> LENGTH: 22
<212> TYPE: DNA
<213> ORGANISM: Artificial
<220> FEATURE:
<223> OTHER INFORMATION: Synthetic DNA

<400> SEQUENCE: 41
aactatacaa tctactacct ca                                             22

<210> SEQ ID NO 42
<211> LENGTH: 21
<212> TYPE: DNA
<213> ORGANISM: Artificial
<220> FEATURE:
<223> OTHER INFORMATION: Synthetic DNA

<400> SEQUENCE: 42
actgtacaaa ctactacctc a                                              21
```

METHOD OF DETECTING NUCLEIC ACID BY USING NUCLEIC ACID MICROARRAY

CROSS REFERENCE TO PRIOR APPLICATION

This is a U.S. national phase application under 35 U.S.C. §371 of International Patent Application No. PCT/JP2006/302402 filed Feb. 6, 2006 and claims the benefit of Japanese Application No. 2005-028843 filed Feb. 4, 2005, both of them are incorporated by reference herein. The International Application was published in Japanese on Aug. 10, 2006 as WO 2006/083040 a1 under PCT article 21(2).

TECHNICAL FIELD

The present invention relates to a method of detecting a nucleic acid by a hybridization technique using a nucleic acid microarray.

BACKGROUND ART

A nucleic acid microarray includes a substrate and a great number of nucleic acid probes independently immobilized on the substrate. As the nucleic acid probe, cDNA or a synthetic oligonucleic acid is often used. A conventionally used microarray includes a surface-treated substrate formed of glass, silicon or the like and nucleic acid probes immobilized thereon. Recently, substrates having an improved property, for example, a gel substrate, have been used.

A method of detecting a nucleic acid by a hybridization technique is performed as follows. To nucleic acid probes immobilized to a nucleic acid microarray, nucleic acid samples, which are to be examined, are hybridized sequence-specifically. Hybrids formed by the sequence-specific hybridization are detected with a fluorescent substance or the like, and molecules having nucleotide sequences in the samples corresponding to the plurality of nucleic acid probes are examined quantitatively or qualitatively. This method is used for analyzing, for example, the expression amount of a plurality of nucleotide sequences or the sequence itself of a specific nucleotide sequence.

Conventionally, nucleic acids are detected as follows. A hybridization reaction is caused under appropriate preset conditions, and nucleic acid samples and other unnecessary substances remaining on the surface of the array are removed by washing. Thus, nucleic acid samples which form specific hybrids with the nucleic acid probes are detected. A nucleic acid probe is often designed to be complementary or identical to a nucleotide sequence desired to be detected and used for the purpose of sequence analysis, function analysis or the like. As the nucleic acid probe, a nucleic acid having a relatively long chain such as cDNA or the like, a synthetic oligonucleic acid having a relatively short chain, or the like is used. In the case where a synthetic oligonucleic acid is used as the nucleic acid probe for detecting a nucleic acid of human, mouse or other biological organism, for which the findings of gene information are accumulated, the base sequence information thereof is usable. Using such base sequence information, and in consideration of the homology or the function of the base sequence, etc., the sequence of a synthetic oligonucleic acid is designed. Thus, a nucleic acid probe can be produced.

DISCLOSURE OF THE INVENTION

The nucleic acid probes to be immobilized on the same microarray need to be adjusted to have a uniform Tm value (the temperature at which the nucleic acid double strand is dissociated into single strands) such that each nucleic acid probe is suitable to the hybridization conditions with the nucleic acid sample and to the washing conditions. However, the nucleotide sequences of a biological organism may include a plurality of similar sequences. It is difficult to design a nucleic acid probe for detecting a region having a low sequence specificity or a region having an unbalanced GC content. Even if such a nucleic acid probe is designed, it is difficult to obtain accurate data using a nucleic acid microarray having such a nucleic acid probe immobilized thereon.

In order to solve this problem, it has been studied to use, for example, optimum hybridization conditions and washing conditions to detect a nucleic acid (Japanese Laid-Open Patent Publication No. 2003-000300). According to this technique, the detection is performed as follows. A plurality of types of nucleic acid probes having the same base sequence are immobilized on a nucleic acid microarray, and the temperature of the microarray is changed in a graded manner. Then, the signal strength is compared among the plurality of types of nucleic acid probes having the same base sequence. However, this method is not easily performed because only the temperature is used as the parameter for determining the hybridization conditions and a special apparatus is necessary.

The object of the present invention is a method of detecting a nucleic acid that is not restricted by the design of the base sequence of a nucleic acid probe.

As a result of active studies for solving the above-described problems, the present inventor found that by repeating washing and detection in multiple stages, the precision of sequence-specific hybridization can be improved stepwise, and restrictions in designing the nucleic acid probes, in particular, restrictions on the Tm value and the sequence length of the nucleic acid probes can be eased; and thus completed the present invention.

The present invention is directed to a method of detecting a nucleic acid, comprising the following steps:

(1) contacting a solution containing nucleic acid samples with a nucleic acid microarray, including a plurality of nucleic acid probes which are independently immobilized, and causing a hybridization reaction of the probes and nucleic acids in the nucleic acid samples; and (2) washing nucleic acid hybrids formed on the nucleic acid microarray a plurality of times while changing a washing condition from a level providing a weak washing effect to a level providing a strong washing effect and performing a detection operation of a nucleic acid hybrid each time the washing is performed.

To change the washing conditions, changes of the salt concentration of a washing solution, changes of a washing solution temperature, or a combination thereof may be used.

BRIEF DESCRIPTION OF THE DRAWINGS

FIG. 2 shows a design of a nucleic microarray.

DESCRIPTION OF THE REFERENCE NUMERALS

Figure 1:
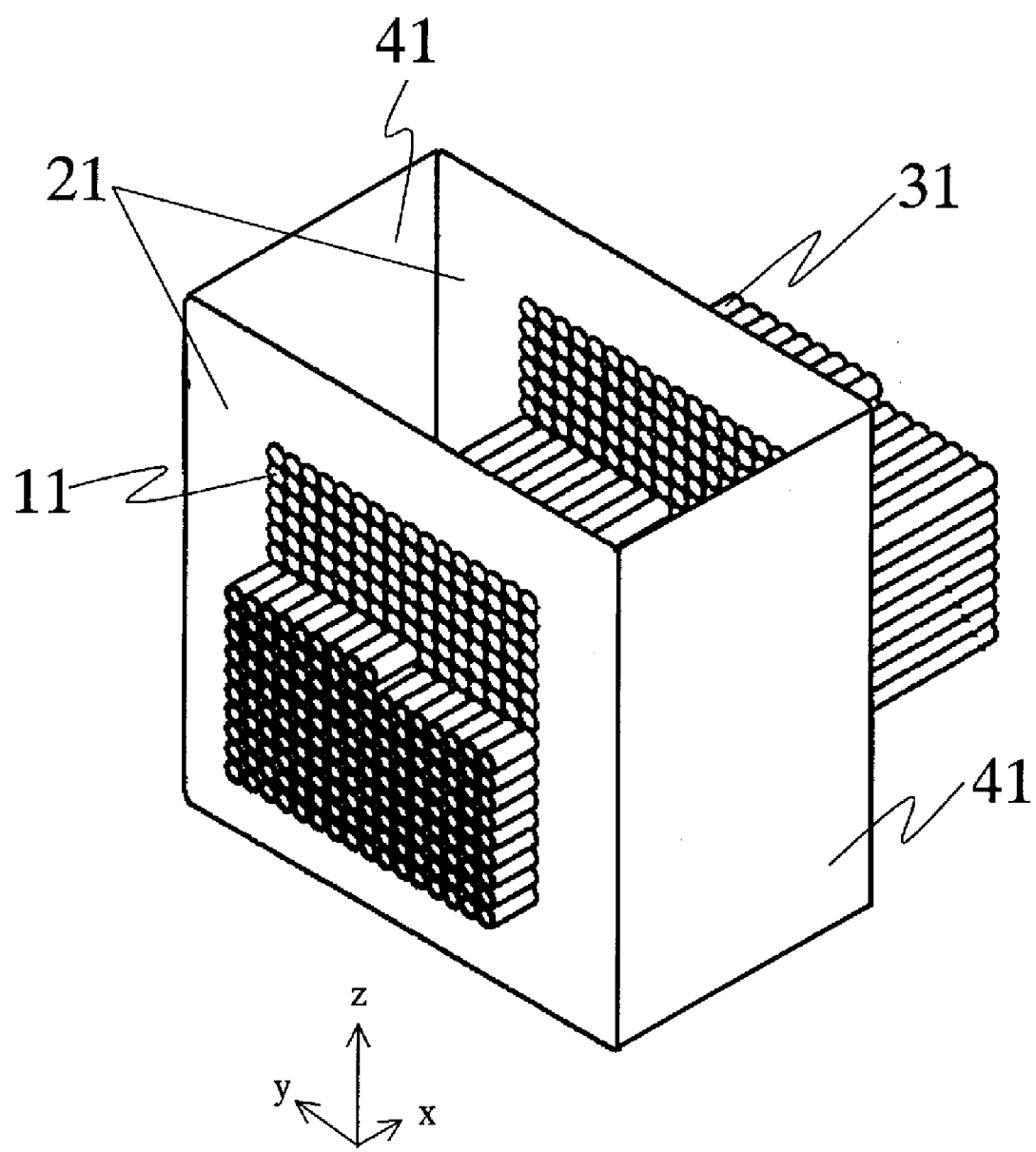
FIG. 1 shows an arrangement immobilization device for producing a fiber arranged body.

11 ... pore
21 ... porous plate
31 ... hollow fiber
41 ... plate-like body

BEST MODE FOR CARRYING OUT THE INVENTION

Hereinafter, embodiments of the present invention will be described. The following embodiments are given in order to illustrate the present invention and are not intended to limit the present invention in any way. The documents, laid-open publications, patents and other patent documents cited in this specification are incorporated herein by reference.

The present invention is directed to a method of detecting a nucleic acid, comprising a first step of contacting a solution containing nucleic acid samples with a nucleic acid microarray, including a plurality of nucleic acid probes which are independently immobilized, and causing a hybridization reaction of the probes and nucleic acids comprising base sequences complementary to the probes in the nucleic acid samples; and a second step of washing nucleic acid hybrids formed on the nucleic acid microarray a plurality of times while changing a washing condition from a level providing a weak washing effect to a level providing a strong washing effect and performing a detection operation of a nucleic acid hybrid each time the washing is performed.

In the first step, a solution containing nucleic acid samples is contacted with a nucleic acid microarray including a plurality of nucleic acid probes which are independently immobilized, and a hybridization reaction of the probes and nucleic acids in the nucleic acid samples (for example, nucleic acids comprising base sequences complementary to the probes) is caused.

The term "nucleic acid probe" refers to a nucleic acid comprising a base sequence complementary to a gene sequence to be detected. A nucleic acid probe may be designed using, for example, commercially available probe designing software or the like. As the designed nucleic acid probe, a synthetic oligonucleic acid is preferably used from the viewpoints of the sequence specificity, the detection accuracy and the stability of the hybridization, although there is no specific limitation on the type or production method of the nucleic acid probe.

Each prepared nucleic acid probe is independently located on an appropriate substrate. The term "independently" refers to the state where each probe is located physically isolated from other probes. For example, in the case where the substrate is a flat substrate, the term "independently" refers to the state where the probes are located away from the other probes with a certain interval on the flat substrate. In the case where the substrate is a collection of strip-like elements, the term "independently" refers to the state where one type of probe is located on one strip.

As the substrate, a flat substrate formed of glass, silicon, a resin or the like is usable, for example. When a flat substrate is used, the nucleic acid probes may be immobilized by, for example, photolithography or spotting.

As the substrate, a substrate having through-holes may be used instead of a flat substrate. In this case, the nucleic acid probes may be immobilized on an inner surface of the through-holes. Alternatively, a gel is retained in the through-holes and the nucleic acid probes may be retained in the gel.

Now, a nucleic acid microarray including hollow fibers as a material for forming the through-holes, a gel retained in each hollow portion thereof, and nucleic acid probes retained in the gel will be described in detail. This nucleic acid microarray can be produced by, for example, the following steps a) through d):

a) the step of arranging a plurality of hollow fibers three-dimensionally such that longitudinal sides thereof are directed in the same direction to produce arranged bodies;

b) the step of embedding the arranged bodies to produce a block;

c) the step of introducing a gel precursor polymerizable solution containing nucleic acid probes into the hollow portions of the hollow fibers in the block and causing a polymerization reaction to retain a gel-like substance containing the nucleic acid probes in the hollow portions; and d) the step of cutting the block in a direction crossing a longitudinal direction of the hollow fibers to obtain thin pieces.

Examples of materials usable as the hollow fibers include polyamide-type hollow fiber such as nylon 6, nylon 66, aromatic polyamide and the like; polyester-type hollow fiber such as polyethylene terephthalate, polybutylene terephthalate, polylactic acid, polyglycolic acid, polycarbonate and the like; acrylic-type hollow fiber such as polyacrylonitrile and the like; polyolefin-type hollow fiber such as polyethylene, polypropylene and the like; polymethacrylic-type hollow fiber such as methyl polymethacrylate and the like; polyvinyl alcohol-type hollow fiber; polyvinylidene chloride-type hollow fiber; polyvinyl chloride-type hollow fiber; polyurethane-type hollow fiber; phenol-type hollow fiber; fluorine-type hollow fiber such as polyvinylidene fluoride, polytetrafluoroethylene and the like; polyalkyleneparaoxybenzoate-type hollow fiber; and the like.

The hollow fibers are arranged three-dimensionally such that the longitudinal sides thereof are directed in the same direction. According to an arranging method, for example, a plurality of hollow fibers are located parallel to each other with a predetermined interval on a sheet-like element such as a tacky sheet or the like to obtain a sheet, and then the sheet is rolled up spirally (see Japanese Laid-Open Patent Publication No. 11-108928). According to another arranging method, two porous plates each having a plurality of pores at a predetermined interval are stacked such that the plates have the pores at matched positions. The hollow fibers are inserted through the pores, and the two porous plates are distanced from each other. Areas round the fibers in a space between the two plates are filled with a curable resin material, and the resin is cured (see Japanese Laid-Open Patent Publication No. 2001-133453).

Next, the arranged bodies are embedded such that the arrangement is not disturbed. The encapsulation may be performed by, for example, injecting a polyurethane resin, an epoxy resin or the like into the inter-fiber spaces or by bonding the fibers by thermal fusion.

Then, a gel precursor polymerizable solution containing the nucleic acid probes is introduced into the hollow portions of the hollow fibers in the embedded arranged body to cause a polymerization reaction in the hollow portions. Thus, the gel is retained in the hollow portions, and the nucleic acid probes are immobilized in the gel.

The gel precursor solution contains, for example, at least one type of monomer such as acrylamide, N,N-dimethylacrylamide, N-isopropylacrylamide, N-acryloylaminoethoxyethanol, N-acryloylaminopropanol, N-methylolacrylamide, N-vinylpyrrolidone, hydroxyethylmethacrylate, (meth)acrylic acid, allyldextrine or the like; and methylenebis(meth)

acrylamide, polyethyleneglycoldi(meth)acrylate or the like as a crosslinking monomer. Where a terminus of the nucleic acid probe is pre-modified with an unsaturated functional group, the nucleic acid probe is copolymerized with the gel precursor via the terminus and thus the nucleic acid probe is chemically bound to the structure of the gel (see Japanese Laid-Open Patent Publication No. 2004-163211).

Next, the resultant block is cut in a direction crossing the longitudinal direction of the hollow fibers to obtain thin pieces. The thin pieces produced here are each usable as a nucleic acid microarray for the present invention. The thickness of each nucleic acid microarray is about 0.1 mm to 1 mm. The block may be cut by, for example, a microtome, a laser or the like.

The nucleic acid microarray prepared as described above is put into contact with a solution containing nucleic acid samples, and a hybridization reaction is caused between the nucleic acid probes and the nucleic acids comprising complementary base sequences to the probes in the nucleic acid samples.

Examples of materials usable as the nucleic acid samples include nucleic acids comprising a base sequence complementary to the nucleic acid probes, nucleic acids comprising no base sequence complementary to the nucleic acid probes, and a combination thereof. A nucleic acid sample may be prepared using PCR, reverse transcription reaction, transcription reaction or the like regardless of the type or origin, for example, regardless of whether the nucleic acid sample is a DNA or RNA; but the preparation method is not limited to these. As a generally known method for preparing a nucleic acid sample, a method described in a commercially available textbook "Molecular Cloning (CSHL PRESS)" may be used. The nucleic acid sample may be appropriately labeled for detection. Examples of usable labeling materials include fluorescent substances, radioisotopes, and enzymes. The labeling may be performed by, for example, a technique described in "Nucleic Acid Microarray and the Latest PCR Method (published by Shujunsha)".

The term "contact" refers to putting all or a part of the probes arranged in the microarray into a state of being immersed in a hybridization solution containing nucleic acid samples. The hybridization reaction is caused by preparing a hybridization solution containing nucleic acid samples and contacting the hybridization solution with the nucleic acid microarray on which nucleic acid probes are immobilized. For example, a technique described in a commercially available textbook "Nucleic Acid Microarray and the Latest PCR Method (published by Shujunsha)" is usable.

Factors determining the conditions of the hybridization reaction include, for example, the temperature at the time of the reaction, and the salt concentration and the pH value of the hybridization solution. A condition is preferably selected as the temperature and the salt concentration of the hybridization solution, which is sufficient for at least the specific nucleic acids to form nucleic acid hybrids with the nucleic acid probes in the sample solution which contains both the specific nucleic acids which comprise complementary base sequences to the nucleic acid probes and non-specific nucleic acids which do not comprise such complementary base sequences to the nucleic acid probes. The conditions may be determined by, using the salt concentration of the solution the containing nucleic acid samples dissolved therein as the index, calculating the Tm value from the sequence information on the nucleic acid probes corresponding to the dissolved nucleic acids. Specifically, the calculation expression proposed by Baldino, F. J. et al. (Methods Enzymol. 168:761-777) is usable to calculate an appropriate temperature condition together with the salt concentration of the hybridization reaction solution. The hybridization reaction is preferably caused under the condition in which the reaction temperature is Tm or lower.

In the second step, nucleic acid hybrids formed on the nucleic acid microarray are washed a plurality of times while changing a washing condition from a level providing a weak washing effect to a level providing a strong washing effect.

Usually on the post-hybridization nucleic acid microarray, coexisting contaminants such as non-specific hybrids obtained by non-specific binding with the nucleic acid probes, enzymes mixed in the samples and the like are present as well as the nucleic acid hybrids of the specific nucleic acids and the nucleic acid probes. In order to detect only the specific nucleic acid hybrids, it is necessary to perform a washing operation to remove the coexisting contaminants. Examples of usable washing solutions include SSC solutions and SDS solutions prepared from sodium chloride, sodium citrate or the like, and a mixture of an SSC solution and an SDS solution. A method for preparing such a washing solution is described in, for example, "Biological Experiments Illustrated (published by Shujunsha)".

The washing operation may be performed by, for example, immersing the nucleic acid microarray in a washing solution which is optimized to have a certain salt concentration, temperature, and pH value and contains no nucleic acid sample; or by causing the surface of the nucleic acid microarray or the sites of the nucleic acid microarray, to which the nucleic acid probes are bound, to pass through, or reside in, the washing solution. The washing solution used here needs to have an appropriate salt concentration, temperature and pH value, which are preferably determined using the above-mentioned Tm calculation expression as the index.

In a preferable embodiment of washing, a washing solution is put into a vessel larger than the nucleic acid microarray, and the temperature of the washing solution is kept at a certain level using a thermostat oven or a temperature control device. Then, the nucleic acid microarray is immersed in the washing solution contained in the vessel. Ideally as a result of this washing operation, only the specific nucleic acid hybrids remain while the non-specific hybrids and other coexisting contaminants are all washed away.

During the washing operation, the degree of the washing effect is changed stepwise from a weak level to a strong level (stepwise washing). The term "washing effect" refers to a function of dissociating the nucleic acid hybrids of the nucleic acid samples and the nucleic acid probes. The expression "strong washing effect" refers to a washing effect obtained by, for example, a condition in which the salt concentration of the washing solution is lower than that of the control washing condition, a condition in which the temperature of the washing solution is higher than that of the control washing condition, or a combination thereof. The expression "weak washing effect" refers to a washing effect obtained by, for example, a condition in which the salt concentration of the washing solution is higher than that of the control washing condition, a condition in which the temperature of the washing solution is lower than that of the control washing condition, or a combination thereof.

Specifically, the washing and detection is performed, first under a washing condition suited to the nucleic acid probe having the lowest Tm value among the nucleic acid probes immobilized on the microarray. Then, the washing and detection is repeated while changing the washing condition stepwise up to a condition suited to the nucleic acid probe having the highest Tm value. Notably, when the target nucleic acid is confirmed to have been detected, it is not necessary to continue the stepwise washing and detection until the condition suited to the nucleic acid probe having the highest Tm value. The washing operation can be terminated in the middle. By performing the washing and detection a plurality of times in this manner, it is made possible to, for example, detect nucleic acid hybrids having a dissociation condition proximate to each washing condition separately.

The washing effect depends on, for example, the salt concentration, temperature and amount of the washing solution and the washing time period. Especially, the influence of the salt concentration and temperature on the washing effect is defined in accordance with the relationship with the base composition of the nucleic acid probe.

The washing condition is changed stepwise by, for example, changing the temperature of the washing solution stepwise while maintaining the salt concentration. Specifically, a salt concentration is first selected arbitrarily (from the range to which the Tm calculation expression is applicable). Next, the probe having the lowest Tm value among all the nucleic acid probes immobilized on the nucleic acid microarray is found based on the Tm calculation expression. The lowest Tm value, or preferably a temperature lower by 1° C. or greater than the lowest Tm value, is selected as the washing condition of the washing solution for the first stage. Then, the temperature of the washing solution is raised stepwise. The washing operation is performed at least once at raised temperatures. The temperature of the washing solution for the second stage et seq. merely needs to be higher than the temperature of the washing solution in the immediately previous stage, and there is no specific limitation on the degree of temperature rise. The temperature of the washing solution may be, for example, raised up to a temperature which is equal to or higher than the highest Tm value among those of the probes immobilized on the array, preferably a temperature which is higher by 1° C. or greater than the highest Tm value.

Alternatively, the washing condition may be changed stepwise by changing the salt concentration of the washing solution stepwise while maintaining the temperature thereof. Specifically, a temperature of the washing solution is first selected arbitrarily (from the range of temperature which can be obtained from the range of salt concentration to which the Tm calculation expression is applicable). Next, the probe having the lowest Tm value among all the nucleic acid probes immobilized on the nucleic acid microarray is found based on the Tm calculation expression. A salt concentration of the washing solution, at which the lowest Tm value is equal to, or preferably higher by 1° C. or greater than, the defined temperature of the washing solution, is selected as the washing condition for the first stage. Then, the salt concentration of the washing solution is reduced stepwise. The washing operation is performed at least once at reduced salt concentrations. The salt concentration of the washing solution for the second stage et seq. merely needs to be lower than the salt concentration of the washing solution in the immediately previous stage, and there is no specific limitation on the degree of salt concentration drop. The salt concentration of the washing solution is, for example, may be reduced down to a salt concentration, at which the highest Tm value of those of the probes immobilized on the microarray is lower by, preferably, 1° C. or greater than the defined temperature of the washing solution.

The washing condition may be changed to a level providing a stronger effect stepwise by, for example, changing the temperature and the salt concentration of the washing solution in combination. As long as the washing effect is changed stepwise, either one of, or both of, the temperature and the salt concentration of the washing solution may be changed in each stage of the washing operation.

The salt concentration of the washing solution can be more easily controlled than the temperature of the washing solution. From this viewpoint, it is preferable to change the salt concentration of the washing solution stepwise. Example 1 shows a specific example of the method of changing the salt concentration of the washing solution stepwise. Example 2 shows a specific example of the method of changing the temperature of the washing solution stepwise.

The Tm value of each probe where the salt concentration is fixed, and the salt concentration where the Tm value of each probe is fixed, can be calculated using a known calculation expression based on the GC content and the base sequence length of the corresponding probe, but the calculation expression is not limited on any specific calculation expression.

It is also possible to use additives including a surfactant and a denaturing agent in order to change the washing degree.

In the second step, a detection operation of a nucleic acid hybrid is performed each time the washing operation is performed. Any of various methods is usable to perform the detection operation of a nucleic acid hybrid after the washing operation. Examples of usable methods include a fluorescent labeling detection method, a chemiluminescent method, a radioisotope method and the like. According to a fluorescent labeling detection method, a fluorescent signal of a pre-labeled nucleic acid sample, or a fluorescent signal of a nucleic acid labeled with an intercalator after the hybridization, may be detected.

The fluorescent signal may be detected by a fluorescent microscope equipped with, for example, a cooled CCD camera, a filter allowing only excited light to pass therethrough, a filter allowing only fluorescent light to pass therethrough, an excitation light source, an appropriate optical system, or any other device suitable to detect a fluorescent signal in a microarray. Examples of other usable detection devices include a laser scanner and the like.

It is preferable to perform the detection operation at least in an environment where moisture vaporization is little in order to prevent the surface of the nucleic acid microarray or the entire microarray from being dried. The microarray can be prevented from being dried, for example, by immersing the post-washing nucleic acid microarray to be detected in the solution contained in a vessel to detect the hybrids in a liquid phase, or by enclosing the nucleic acid microarray to be detected in a sealed vessel having a saturated water vapor atmosphere with no moisture vaporization to detect the hybrids.

The above-described detection method is usable for, for example, analysis of the expression amount of transcription products, analysis of the base sequences of genes, analysis of nucleic acid modification or the like.

The analysis of the expression amount of transcription products is to analyze the amount of RNA present inside or outside cells, regardless of whether the biological organism is dead or alive. A single or a plurality of nucleic acid samples are each labeled with a labeling substance independently to cause hybridization in a single or mixed state. Thus, the relative amount ratio among the plurality of nucleic acid samples of RNA is checked. By using the detection method according to the present invention for the analysis, the accuracy of the relative amount ratio among the nucleic acid probes can be improved.

The analysis of the base sequences of genes is to identify the polymorphism, mutation or the like of a nucleotide sequence or to determine the base sequence itself. By using the detection method according to the present invention for the analysis, the identification capability or determination capability for each nucleic acid probe can be improved.

The analysis of the nucleic acid modification is to, for example, examine whether or not the CpG island has been methylated. By using the detection method according to the present invention for the analysis, whether or not the site to be examined has been methylated can be accurately determined in each nucleic acid probe.

The detection method according to the present invention is useful to analyze a short nucleic acid such as microRNA (miRNA) or the like using a microarray. The nucleic acid length of miRNA is about 20 mer. Therefore, it is difficult to uniformize the Tm value of the nucleic acid probes in the microarray for miRNA. The Tm value may be uniformized by introducing a linker to the probe, but the introduction of the linker raises the cost. Thus, the detection method according to the present invention by which the washing strength is changed stepwise to perform a detection operation of nucleic acid hybrids under each level of washing condition is useful to analyze a short nucleic acid such as miRNA or the like.

Now, the present invention will be described specifically by way of examples. The examples show models which clearly demonstrates the consistency of the logic of the present invention, and the present invention is not limited to the following examples.

Example 1

1. Preparation of Nucleic Acid Samples

A Cy5-labeled oligonucleotide having a sequence of each of SEQ ID NO 1 through NO 10 below was synthesized, and an oligonucleotide nucleic acid sample solution containing an equivalent amount of each Cy5-labeled oligonucleotide was produced. Each solution contains 10 fmol/μl of the respective Cy5-labeled oligonucleotide, 2×SSC (sodium chloride: 33.3 mM, sodium citrate: 33.3 mM, pH7.0) and 0.2% SDS (sodium dodecyl sulfate). These oligonucleotides described above were used as model nucleic acid samples.

```
SEQ ID NO 1:
cggattaggg cgttttttat tttcgtcggg agttcgtcga ttggttgggt gtgggcgtac gtgatc SEQ ID NO 2:
cgtttttggt gagcgtcgtc gttagttaat cgcgggggcgt agaggttttt ggtttcgttt cgc SEQ ID NO 3:
cggcgtgggt gtggggcgag tgggtgtgtg cggggtgtgc gcggtagagc gcgttagc SEQ ID NO 4:
cgggggggcgg tgtttcgggg tttatttggt tgtagttacg tatttttttt tagtggcgtc SEQ ID NO 5:
cgcgcgttcg tcgttcgtta tatatcgttc gtagtattcg tgtttagttt cgtagtggcg tttgacgtcg cgttcgc SEQ ID NO 6:
cggatcgagt gcgttcggcg gttgcggaga ggggtagagt aggtagcggg cggc SEQ ID NO 7:
cgcgtggtgt tttgcggtcg tcgtcgttgt ggtcgttcgg ggtggggtgt gaggagggga c
```

-continued
```
SEQ ID NO 8:
cggttggggt ttcgcgttta tacggttttt ggcggggggtt cgcgcgtttc gggagtttcg c SEQ ID NO 9:
cggagcgacg cgtcgtatag ttaatcggcg gagtttttat cgcgggtatt tcggtggcgt tcgc SEQ ID NO 10:
cgcgggcggc gtcgtcgaac gttagcgtta gggggcgggg tgggggaggg agcgaggttt ttc
```

2. Preparation of Nucleic Acid Probes

Ten types of nucleic acid probes (SEQ ID NO 11 through NO 20) which have the same chain lengths and are completely complementary to the ten types of Cy5-labeled oligonucleotides above (SEQ ID NO 1 through NO 10) respectively were synthesized.

```
SEQ ID NO 11:
gatcacgtac gcccacaccc aaccaatcga cgaactcccg acgaaaataa aaaacgccct aatccg SEQ ID NO 12:
gcgaaacgaa accaaaaacc tctacgcccc gcgattaact aacgacgacg ctcaccaaaa acg SEQ ID NO 13:
gctaacgcgc tctaccgcgc acaccccgca cacacccact cgccccacac ccacgccg SEQ ID NO 14:
gacgccacta aaaaaaaata cgtaactaca accaaataaa ccccgaaaca ccgcccccccg SEQ ID NO 15:
gcgaacgcga cgtcaaacgc cactacgaaa ctaaacacga atactacgaa cgatatataa cgaacgacga acgcgcg SEQ ID NO 16:
gccgcccgct acctactcta ccccctctccg caaccgccga acgcactcga tccg SEQ ID NO 17:
gtcccctcct cacacccac cccgaacgac cacaacgacg acgaccgcaa aacaccacgc g SEQ ID NO 18:
gcgaaactcc cgaaacgcgc gaaccccccgc caaaaaccgt ataaacgcga aaccccaacc g SEQ ID NO 19:
gcgaacgcca ccgaaatacc cgcgataaaa actccgccga ttaactatac gacgcgtcgc tccg SEQ ID NO 20:
gaaaaacctc gctccctccc ccaccccgcc ccctaacgct aacgttcgac gacgccgccc gcg
```

Ten types of nucleic acid probes (SEQ ID NO 21 through NO 30) which have the same chain lengths and are partially complementary to the ten types of Cy5-labeled oligonucleotides (SEQ ID NO 1 through NO 10) respectively were synthesized.

These nucleic acid probes were obtained by substituting guanine bases of the base sequences of SEQ ID NO 11 through NO 20 with adenine bases. These nucleic acid probes form non-complementary base pairs with the oligonucleotides as the model nucleic acid samples only at the substituted sites.

```
SEQ ID NO 21:
aatcacatac acccacaccc aaccaatcaa caaactccca acaaaaataa aaaacaccct aatcca SEQ ID NO 22:
acaaaacaaa accaaaaacc tctacaccccc acaattaact aacaacaaca ctcaccaaaa aca SEQ ID NO 23:
actaacacac tcatccacac acaccccaca cacacccact caccccacac ccacacca SEQ ID NO 24:
aacaccacta aaaaaaaata cataactaca accaaataaa ccccaaaaca ccaccccccca SEQ ID NO 25:
acaaacacaa catcaaacac cactacaaaa ctaaacacaa atactacaaa caatatataa caaacaacaa acacaca SEQ ID NO 26:
accacccact acctactcta ccccctatcca caaccaccaa acacactcaa tcca SEQ ID NO 27:
atcccctcct cacacccccca cccaaacaac cacaacaaca acaaccacaa aacaccacac a SEQ ID NO 28:
acaaaactcc caaaacacac aaacccccac caaaaaccat ataaacacaa aacccccaacc a SEQ ID NO 29:
acaaacacca ccaaaatacc cacaataaaa actccaccaa ttaactatac aacacatcac tcca SEQ ID NO 30:
aaaaaacctc actccctccc ccaccccacc ccctaacact aacattcaac aacaccaccc aca
```

Regarding the base sequences represented by SEQ ID NO 1 through NO 30, for example, SEQ ID NO 11 is completely complementary to SEQ ID NO 1, and SEQ ID NO 21 is obtained by substituting guanine bases in SEQ ID NO 11 with adenine bases. SEQ ID NO 2 through NO 10, SEQ ID NO 12 through NO 20 and SEQ ID NO 22 through NO 30 have the same relationship respectively.

3. Production of Nucleic Acid Microarrays

A bundle of hollow fibers (31) was produced using a sequence immobilization device shown in FIG. 1. In the figure, letters x, y and z represent three-dimensional axes perpendicular to one another, and the x axis matches the longitudinal direction of the fibers.

First, two porous plates (21) each having a thickness of 0.1 mm and having 144 pores (11) of a diameter of 0.32 mm formed therein were prepared. The pores (11) were arranged in 12 rows by 12 columns, and the distance between the centers of each two adjacent pores (11) was 0.42 mm. These porous plates were stacked, and one polycarbonate hollow fiber (31) (produced by Mitsubishi Engineering-Plastics Corporation; having 1% by mass of carbon black added thereto) was inserted into each of all the pores.

The two porous plates were moved away from each other in the state where a tensile force of 0.1 N was applied to each fiber in the x axis direction, and the two porous plates were respectively fixed at two positions, i.e., a position of 20 mm away from one end of the hollow fibers and at a position of 100 mm away from the one end of the hollow fibers. Namely, the two plates were separated from each other by 80 mm.

Next, the space between the two porous plates was enclosed by a plate-like body (41) on three sides thereof. Thus, a vessel which is open only at the top is obtained.

Then, a resin material was injected into the vessel from the top opening. As the resin material, a polyurethane resin adhesive (Nipporan 4276, Coronate 4403, produced by Nippon Polyurethane Industry Co., Ltd.) having 2.5% by mass of carbon black added thereto with respect to the total amount of the adhesive was used. The resin material was kept still at 25° C. for 1 week to be cured. Then, the porous plates and the plate-like body were removed to obtain a hollow fiber bundle.

Next, a gel precursor polymerizable solution containing the monomers and the initiator mixed at the mass ratio shown in Table 1 was prepared.

TABLE 1

| Composition | Mass ratio (concentration is shown for the nucleic acid probe) |
|---|---|
| N,N-dimethylacrylamide | 3.42% |
| N,N-methylenebisacrylamide | 0.38% |
| 2,2'-azobis[2-(2-imidazoline-2-yl)propane]-dihydrochloride (VA-044) | 0.1% |
| Water | 96.1% |
| Nucleic acid probe (SEQ ID NO 11 through NO 30) | 5 mol/μl |

Next, the gel precursor polymerizable solution containing the nucleic acid probes was set in a desiccator. After the inner pressure of the desiccator was set to a reduced level, one end of the hollow fiber bundle which is not fixed was immersed in the solution. Nitrogen gas was injected into the desiccator, and the gel precursor polymerizable solution containing the capture probes was introduced into the hollow portions of the hollow fibers. Then, the temperature inside the vessel was set to 70° C., and the polymerization was allowed to proceed for 3 hours.

Thus, a hollow fiber bundle having the nucleic acid probes retained in the hollow portions of the hollow fibers by the gel-type material was obtained.

The obtained hollow fiber bundle was sliced in a direction perpendicular to the longitudinal direction of the fibers using a microtome to produce 50 thin sheets (DNA microarrays) each having a thickness of 0.5 mm. The concentration of the nucleic acid probes present in the hollow portions was 50 fmol/spot. FIG. 2 shows the design of the obtained nucleic acid microarray. In FIG. 2, the numerals represent the sequence numbers of the nucleic acid probes, and letter B represents blank gel (gel which contains no nucleic acid probe).

4. Hybridization Reaction, and Washing and Detection Operation

The nucleic acid microarrays produced in section 3 above were put into contact with the oligonucleotide solutions containing the labeled oligonucleotides prepared in section 1 above to cause hybridization at 75° C. for 3 hours in a thermostat oven.

After the hybridization, the microarrays were washed in 1×SSC at 75° C. for 20 minutes, immersed in 1×SSC, and covered with a glass cover. Then, the fluorescent signal strength of each labeled nucleic acid sample molecule was measured using an automatic nucleic acid microarray detector of a cooled CCD camera system. The measurement results are shown in FIG. 3.

Figure 4:
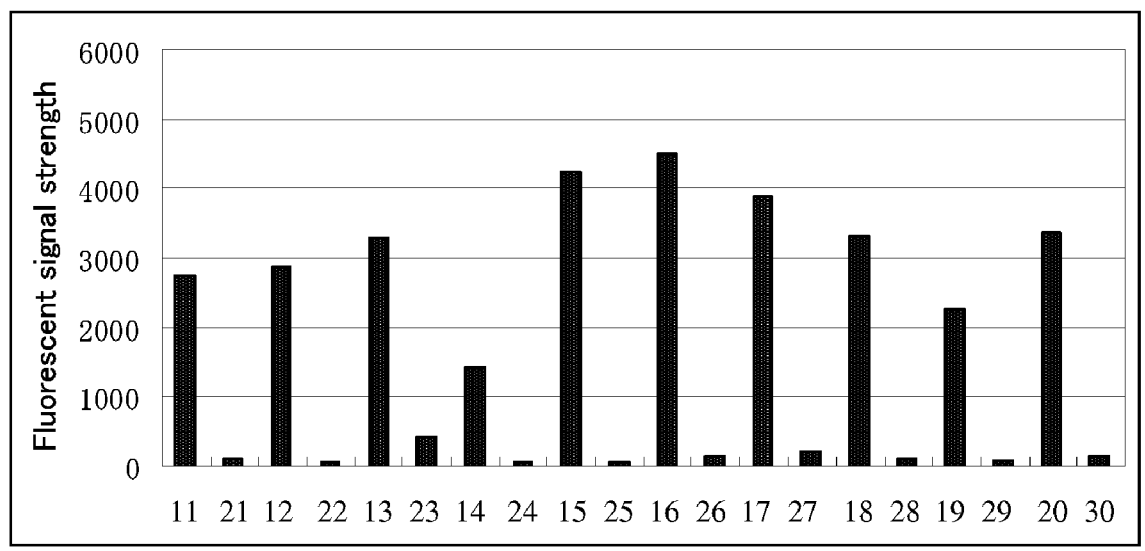
FIG. 4 shows the signal strength for nucleic acid detection after the nucleic acid microarrays are further washed in 0.7× SSC at 75° C. for 20 minutes.

After this, the microarrays were washed in 0.7×SSC at 75° C. for 20 minutes, immersed in 0.7×SSC, and covered with a glass cover. Then, the fluorescent signal strength of each labeled nucleic acid sample molecule was measured using an automatic nucleic acid microarray detector of a cooled CCD camera system. The measurement results are shown in FIG. 4.

In this example, the nucleic acids of the SEQ ID NO 1 through NO 10 contained in the nucleic acid samples are all complementary to the nucleic acid probes of SEQ ID NO 11 through NO 20, and are partially complementary to the nucleic acid probes of SEQ ID NO 21 through NO 30. Therefore, it is expected that the fluorescent signal of a zone in which the nucleic acid probes of SEQ ID NO 11 through NO 20 are immobilized is stronger than the fluorescent signal of a zone in which the nucleic acid probes of SEQ ID NO 21 through NO 30 are immobilized. In more detail, it is expected that a fluorescent signal is detected in the zone in which the nucleic acid probes of SEQ ID NO 11 through NO 20 are immobilized while no fluorescent signal is detected in the zone in which the nucleic acid probes of SEQ ID NO 21 through NO 30 are immobilized, or that the fluorescent signal strength of the zone in which the nucleic acid probes of SEQ ID NO 21 through NO 30 are immobilized is significantly lower than the fluorescent signal strength of the zone in which the nucleic acid probes of SEQ ID NO 11 through NO 20 are immobilized.

Figure 3:
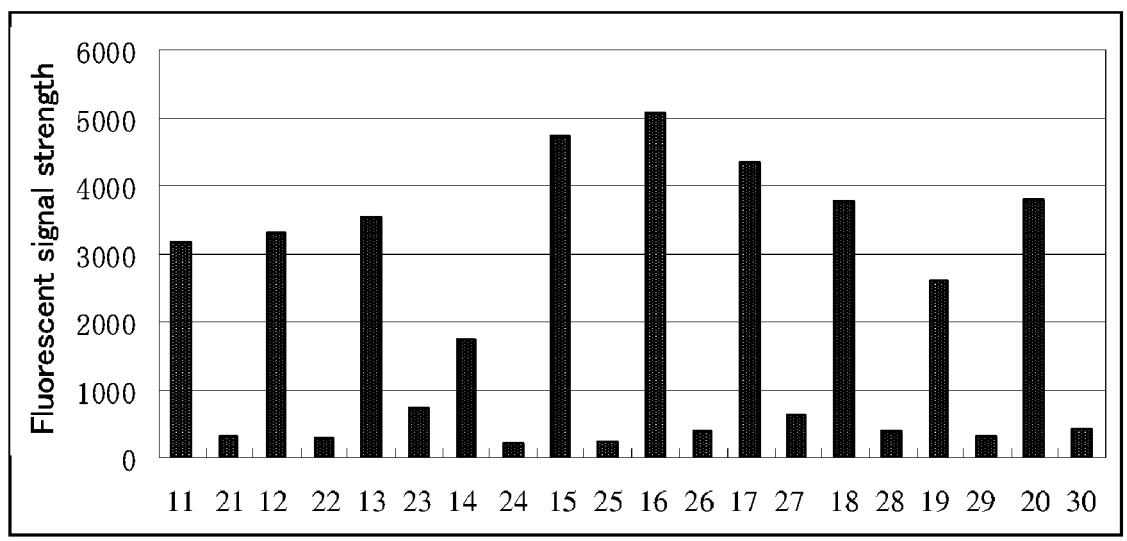
FIG. 3 shows the signal strength for nucleic acid detection after the nucleic acid microarrays are washed in 1×SSC at 75° C. for 20 minutes.

In this example, after the microarrays were washed in 1×SSC at 75° C. for 20 minutes, the fluorescent signal strength of the zone in which the nucleic acid probes of SEQ ID NO 21 through NO 30 were immobilized was slightly strong (see FIG. 3). However, after the microarrays were further washed in 0.7×SSC at 75° C. for 20 minutes, the fluorescent signal strength of the zone in which the nucleic acid probes of SEQ ID NO 21 through NO 30 were immobilized was significantly reduced (see FIG. 4). The fluorescent signal strength of the zone in which the nucleic acid probes of SEQ ID NO 11 through NO 20 was not greatly changed.

From the above, it is proven that the cross-hybridized nucleic acids can be effectively removed by washing the microarrays repeatedly without reducing the fluorescent signal strength of the nucleic acids to be detected.

Example 2

1. Preparation of Nucleic Acid Samples

An oligonucleotides having a sequence of each of SEQ ID NO 31 through NO 36 below was synthesized. Each oligonucleotide was labeled and purified using, and in accordance with the protocol attached to, PlatinumBright™: Nucleic Acid Labeling Kit (produced by KREATECH). Then, a solution containing 10 fmol/l of the respective oligonucleotide, 2×SSC (sodium chloride: 33.3 mM, sodium citrate: 33.3 mM, pH7.0) and 0.2% SDS (sodium dodecyl sulfate) was produced.

```
SEQ ID NO 31:
tgaggtagta ggttgtgtgg tt

SEQ ID NO 32:
tgaggtagta ggttgtatgg tt

SEQ ID NO 33:
agaggtagta ggttgcatag t

SEQ ID NO 34:
tgaggtagga ggttgtatag t

SEQ ID NO 35:
tgaggtagta gattgtatag t

SEQ ID NO 36:
tgaggtagta gtttgtacag t
```

2. Preparation of Nucleic Acid Probes

Six types of nucleic acid probes (SEQ ID NO 37 through NO 42) which are completely complementary to the six types of oligonucleotides above (SEQ ID NO 31 through NO 36) respectively were synthesized. SEQ ID NO 37 is completely complementary to SEQ ID NO 31. SEQ ID NO 32 through NO 36 and SEQ ID NO 38 through NO 42 have the same relationship respectively. The Tm value was calculated at the salt concentration of 2×SSC in accordance with expression 1 below.

$$81.5+16.6(\log_{10}[Na^+])+0.41(\%[G+C])-600/n \qquad [\text{Expression 1}]$$

These nucleic acid probes each have a very short sequence and are highly homologous to one another, and therefore may possibly easily cross-hybridize with the same nucleic acid sample.

```
SEQ ID NO 37 (Tm = 66° C.):
aaccacacaa cctactacct ca

SEQ ID NO 38 (Tm = 64° C.):
aaccatacaa cctactacct ca

SEQ ID NO 39 (Tm = 64° C.):
actatgcaac ctactacctc t

SEQ ID NO 40 (Tm = 64° C.):
actatacaac ctcctacctc a

SEQ ID NO 41 (Tm = 60° C.):
aactatacaa tctactacct ca

SEQ ID NO 42 (Tm = 62° C.):
actgtacaaa ctactacctc a
```

3. Production of Nucleic Acid Microarrays

Nucleic acid microarrays were produced by the same method as in Example 1 except that the nucleic acid probes of SEQ ID NO 37 through SEQ ID NO 42 were used instead of the nucleic acid probes shown in Table 1 in Example 1.

4. Hybridization Reaction, and Washing and Detection Operation

The nucleic acid microarrays produced in section 3 above were put into contact with the oligonucleotide solutions containing the labeled oligonucleotides prepared in section 1 above to cause hybridization. The condition of the hybridization was 50° C. After the temperature reached 50° C., the resultant microarrays were incubated for 16 hours, and then washed as follows. The microarrays were immersed in a 2×SSC, 0.2% SDS solution at 50° C. for 20 minutes twice, and then immersed in 2×SSC at 50° C. for 10 minutes. After being washed, the microarrays were immersed in 2×SSC and covered with a glass cover. Then, the fluorescent signal strength of each labeled nucleic acid sample molecule was measured using an automatic nucleic acid microarray detector of a cooled CCD camera system. The measurement results are shown in Table 2. Among the fluorescent signals from the hybrids formed in the nucleic acid microarrays, the fluorescent signal from a completely complementary hybrid is shown with a strength value of 100, and the fluorescent signals from the other hybrids are each shown with a strength value as a relative value to 100. A strength value equal to or lower than the lower detection limit is shown as "ND".

TABLE 2

|  | SEQ ID NO 31 | SEQ ID NO 32 | SEQ ID NO 33 | SEQ ID NO 34 | SEQ ID NO 35 | SEQ ID NO 36 |
| --- | --- | --- | --- | --- | --- | --- |
| SEQ ID NO 37 | 100 | 41 | 2 | 1 | ND | ND |
| SEQ ID NO 38 | 67 | 100 | 4 | 9 | ND | ND |
| SEQ ID NO 39 | 9 | 15 | 100 | 9 | ND | ND |
| SEQ ID NO 40 | 0 | 3 | ND | 100 | ND | ND |
| SEQ ID NO 41 | 1 | 9 | ND | 3 | 100 | ND |
| SEQ ID NO 42 | 1 | 3 | ND | 0 | 0 | 100 |

Next, the temperature of 2×SSC was raised to 55° C., and the nucleic acid microarrays were immersed in 2×SSC for 30 minutes. The fluorescent signal strength was measured in the same manner as above. The results are shown in Table 3.

TABLE 3

|  | SEQ ID NO 31 | SEQ ID NO 32 | SEQ ID NO 33 | SEQ ID NO 34 | SEQ ID NO 35 | SEQ ID NO 36 |
| --- | --- | --- | --- | --- | --- | --- |
| SEQ ID NO 37 | 100 | 25 | 0 | ND | ND | ND |
| SEQ ID NO 38 | 50 | 100 | 1 | 3 | ND | ND |
| SEQ ID NO 39 | 2 | 5 | 100 | 2 | ND | ND |
| SEQ ID NO 40 | 0 | 0 | ND | 100 | ND | ND |
| SEQ ID NO 41 | ND | 1 | ND | ND | 100 | ND |
| SEQ ID NO 42 | 0 | 0 | ND | ND | ND | 100 |

Comparing Table 2 and Table 3, it is understood that the hybrids in the zones other than those of the hybrids to be detected, i.e., cross-hybridized nucleic acids are being removed by stepwise washing.

Then, temperature was raised to 60° C. and 65° C., and the same operation was performed. The results at 60° C. are shown in Table 4, and the results at 65° C. are shown in Table 5.

TABLE 4

|  | SEQ ID NO 31 | SEQ ID NO 32 | SEQ ID NO 33 | SEQ ID NO 34 | SEQ ID NO 35 | SEQ ID NO 36 |
| --- | --- | --- | --- | --- | --- | --- |
| SEQ ID NO 37 | 100 | 6 | ND | ND | ND | ND |
| SEQ ID NO 38 | 28 | 100 | ND | ND | ND | ND |
| SEQ ID NO 39 | ND | ND | 100 | ND | ND | ND |
| SEQ ID NO 40 | ND | ND | ND | 100 | ND | ND |
| SEQ ID NO 41 | ND | ND | ND | ND | 100 | ND |
| SEQ ID NO 42 | ND | ND | ND | ND | ND | 100 |

TABLE 5

|  | SEQ ID NO 31 | SEQ ID NO 32 | SEQ ID NO 33 | SEQ ID NO 34 | SEQ ID NO 35 | SEQ ID NO 36 |
| --- | --- | --- | --- | --- | --- | --- |
| SEQ ID NO 37 | 100 | 2 | ND | ND | ND | ND |
| SEQ ID NO 38 | ND | 100 | ND | ND | ND | ND |
| SEQ ID NO 39 | ND | ND | 100 | ND | ND | ND |
| SEQ ID NO 40 | ND | ND | ND | 100 | ND | ND |
| SEQ ID NO 41 | ND | ND | ND | ND | 100 | ND |
| SEQ ID NO 42 | ND | ND | ND | ND | ND | 100 |

By setting the washing conditions using the Tm value of each probe as the index, the measurement was carried out with almost no influence of cross-hybridization even for the probes which are highly homologous to one another.

It is understood that in the case of the nucleic acid microarrays in this example, the hybrid of the labeled oligonucleotide of SEQ ID NO 35 and the probe of SEQ ID NO 41 (Tm=60° C.) was detected after being washed at 55° C. with almost no influence of the other cross-hybridized nucleic acids (Table 3).

It is understood that the hybrid of the labeled oligonucleotide of SEQ ID NO 33 and the probe of SEQ ID NO 39 (Tm=64° C.), and the hybrid of the labeled oligonucleotide of SEQ ID NO 34 and the probe of SEQ ID NO 40 (Tm=64° C.), were detected after being washed at 60° C. with no influence of the other cross-hybridized nucleic acids (Table 4).

It is understood that the hybrid of the labeled oligonucleotide of SEQ ID NO 31 and the probe of SEQ ID NO 37 (Tm=66° C.) was detected after being washed at 65° C. with no influence of the other cross-hybridized nucleic acids (Table 5).

Namely, even for separately detecting samples which are very highly homologous to one another, the correspondingly highly homologous probes can be detected with almost no influence of cross-hybridization by performing stepwise washing in accordance with the Tm value of the respective probe-sample combination.

The method according to the present invention is especially useful in case where it is difficult to exhibit the specificity of the probes (for example, for detecting microRNA) in designing probes for a nucleic acid microarray because the sequences to be detected are very short and highly homologous to one another.

INDUSTRIAL APPLICABILITY

The present invention allows a nucleic acid to be detected without being restricted by the design of the base sequence of the nucleic acid probe even where genes immobilized on a microarray are significantly different in the sequence length or the GC content and accordingly the nucleic acid probes are varied in the Tm value estimated based thereon. According to the present invention, a signal derived from sequence-specific hybridization can be easily detected by merely performing a washing operation stepwise in the detection process of the nucleic acid, with no need to use different type of microarrays in accordance with the Tm values or to perform experiments a plurality of times under different hybridization conditions. Namely, the method according to the present invention, by which washing and detection is repeated in multiple stages, can improve the precision of sequence-specific hybridization stepwise and also can ease restrictions in designing the nucleic acid probes, in particular, restrictions on the Tm value (the temperature at which the nucleic acid double strand is dissociated into single strands) or the sequence length of the nucleic acid probes.

The present invention is usable for applications in which base sequences of nucleic acid probes are designed to detect nucleic acid samples, the Tm values of which are not easily uniformized; for example, in applications such as analysis of expression in a focused array in which the genes to be analyzed are narrowed from several hundred types down to several ten types, and disease diagnosis or the like and analysis of short nucleic acids such as miRNA and the like based on the analysis of expression; detection of methylation of nucleic acids; analysis of polymorphism of disease-related genes and gene diagnosis based thereon; typing of pathogens and viruses; and the like. The present invention also improves the reliability of data in these applications.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited are hereby incorporated by reference.

Sequence Listing Free Text

SEQ ID NO 1 through NO 42: synthetic DNA

The invention claimed is:

1. A method of detecting a nucleic acid, comprising the steps of:
   (1) contacting a solution containing nucleic acid samples with a nucleic acid microarray, including a plurality of nucleic acid probes which are independently immobilized, and causing a hybridization reaction of the probes and nucleic acids in the nucleic acid samples; and
   (2) washing nucleic acid hybrids formed on the nucleic acid microarray a plurality of times with a washing solution while changing a condition of the washing solution each time from a level providing a weaker washing effect to a level providing a stronger washing effect and performing a detection operation of a nucleic acid hybrid after each time the washing is performed, wherein each detection operation of a nucleic acid hybrid is performed without drying the nucleic acid microarray.

2. The method according to claim 1, wherein the change of the washing solution condition is a change of salt concentration of a washing solution.

3. The method according to claim 1, wherein the change of the washing solution condition is a change of temperature of a washing solution.

4. The method according to claim 1, wherein the change of the washing solution condition is a change of salt concentration of a washing solution and temperature of the washing solution.

* * * * *